(12) United States Patent
Loeb

(10) Patent No.: US 7,555,347 B2
(45) Date of Patent: Jun. 30, 2009

(54) IDENTIFICATION OF TARGET SITE FOR IMPLANTATION OF A MICROSTIMULATOR

(75) Inventor: Gerald E. Loeb, South Pasadena, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 536 days.

(21) Appl. No.: 11/103,197

(22) Filed: Apr. 11, 2005

(65) Prior Publication Data

US 2005/0245969 A1  Nov. 3, 2005

Related U.S. Application Data

(60) Provisional application No. 60/560,911, filed on Apr. 9, 2004.

(51) Int. Cl.
*A61N 1/08* (2006.01)

(52) U.S. Cl. ............................ 607/60; 600/546

(58) Field of Classification Search ............... 607/46, 607/60, 62, 32, 33, 628; 600/546
See application file for complete search history.

(56) References Cited

U.S. PATENT DOCUMENTS

| | | | |
|---|---|---|---|
| 4,867,164 A * | 9/1989 | Zabara | 607/60 |
| 5,161,533 A | 11/1992 | Prass et al. | |
| 5,193,539 A | 3/1993 | Schulman et al. | |
| 5,193,540 A | 3/1993 | Schulman et al. | |
| 5,284,153 A | 2/1994 | Raymond et al. | |
| 5,284,154 A | 2/1994 | Raymond et al. | |
| 5,312,439 A | 5/1994 | Loeb | |
| 5,324,316 A | 6/1994 | Schulman et al. | |
| 5,545,191 A * | 8/1996 | Mann et al. | 607/60 |
| 5,775,331 A | 7/1998 | Raymond et al. | |
| 5,788,648 A | 8/1998 | Nadel | |
| 6,027,456 A | 2/2000 | Feler et al. | |
| 6,157,861 A * | 12/2000 | Faltys et al. | 607/57 |
| 6,259,945 B1 | 7/2001 | Epstein et al. | |
| 6,298,256 B1 | 10/2001 | Meyer | |
| 6,306,100 B1 | 10/2001 | Prass | |
| 6,325,764 B1 | 12/2001 | Griffith et al. | |
| 6,464,647 B1 | 10/2002 | Angesleva et al. | |
| 6,466,817 B1 | 10/2002 | Kaula et al. | |
| 6,533,732 B1 | 3/2003 | Urmey | |
| 6,547,746 B1 | 4/2003 | Marino | |
| 6,625,481 B2 | 9/2003 | Bennett et al. | |
| 2003/0233125 A1 | 12/2003 | Loeb et al. | |
| 2003/0233126 A1 | 12/2003 | Loeb et al. | |

\* cited by examiner

*Primary Examiner*—George R Evanisko
*Assistant Examiner*—Joseph M Dietrich
(74) *Attorney, Agent, or Firm*—McDermott Will & Emery LLP

(57) ABSTRACT

Devices and methods for locating a target site for the electrical stimulation of muscles are disclosed. The intensity of a search stimulus is varied continuously near the threshold to evoke an M-wave recorded by EMG electrodes. A feedback signal allows the clinician to judge when the threshold is sufficiently low to warrant the implantation of the stimulation electrodes at that site.

7 Claims, 4 Drawing Sheets

IDENTIFICATION OF TARGET SITE FOR IMPLANTATION OF A MICROSTIMULATOR

CROSS-REFERENCE TO RELATED APPLICATIONS

This application claims priority to U.S. Provisional Patent Application 60/560,911 filed Apr. 9, 2004, entitled "Instrumentation and Method of Use to Identify Target Site for Implantation of a Microstimulator,". This application is related to U.S. patent application Ser. No. 10/461,560, filed Jun. 12, 2003, entitled "Injection Devices and Methods for Testing Implants," U.S. patent application Ser. No. 10/461,132, filed Jun. 12, 2003, entitled "Injection Devices and Methods for Unimpeded Target Location Testing," U.S. Provisional Application Ser. No. 60/388,370, filed Jun. 12, 2002, entitled "Method and Apparatus for the Orientation-Specific Delivery of an Implant to Precisely Localized Sites," and U.S. Provisional Application Ser. No. 60/476,007, filed Jun. 4, 2003, entitled "Cargo Delivery Capsule: Method and Apparatus for Precise and Protected Delivery of Cargo into Body Tissues and Cavities." The entire contents of all of these applications are incorporated herein by reference.

BACKGROUND

1. Field

This application relates generally to devices and methods to identify target sites for implantation of microstimulators.

2. General Background and State of the Art

Microstimulators such as the BION® implants are intended to be injected through an insertion tool similar to a large hypodermic needle (Kaplan & Loeb, patent pending). Percutaneous intramuscular wire electrodes are injected similarly through a smaller needle. The target site is usually the nerve entry zone of a specific muscle, since all of the motor axons innervating the muscle fibers will then pass close enough to the stimulation electrodes so that they can be recruited as the stimulus intensity is increased over a reasonable range.

In one approach, the clinician implanting the stimulator typically applies trial stimulation pulses through the tip of the insertion tool in order to determine whether it is located appropriately before releasing the electrodes into the tissue. When the tool is correctly located, the clinician will be able to see or feel a twitch of the correct muscle at a relatively low stimulation pulse intensity called threshold. However, simultaneously moving the tool and adjusting the stimulation intensity to determine this threshold is now difficult to do and usually requires two people and considerable discussion between them. The clinician handling the insertion tool wears sterile gloves and may need both hands to operate the tool and palpate the muscle while an assistant adjusts the stimulation intensity according to verbal instructions.

SUMMARY

In one aspect of the injection devices and systems, a device for identifying a target site for implanting a microstimulator in a body comprises a drape having an aperture; a transmitting antenna attached to the drape that is capable of creating an inductive field to control a microstimulator located within a patient's body; and at least one electromyographic electrode attached to the antenna that is capable of detecting M-waves produced by the patient's body.

In another aspect of the injection devices and systems, a system for identifying a target site for implanting a microstimulator in a body comprises a drape having an aperture; a transmitting antenna attached to the drape that is capable of creating an inductive field to control a microstimulator located within a patient's body; a microstimulator capable of stimulating at least one nerve; at least one electrode capable of detecting M-waves produced by the patient's body; and a controller capable of providing microstimulator-control signals to the transmitting antenna, receiving and analyzing information about the M-waves detected by the at least one electrode, and providing additional signals to the antenna based on the information about the detected M-waves.

In yet another aspect of the injection devices and systems, a method for identifying a target site for implanting a microstimulator in a body comprises inserting a microstimulator injection device containing a microstimulator through a microstimulator-insertion assembly and into a patient's body; providing, through the microstimulator, a stimulation pulse to at least one nerve; detecting, with at least one electrode, at least one M-wave produced by the patient's body; and implanting the microstimulator into the patient's body.

It is understood that other embodiments of the devices and methods will become readily apparent to those skilled in the art from the following detailed description, wherein it is shown and described only exemplary embodiments of the devices, methods and systems by way of illustration. As will be realized, the devices, systems and systems are capable of other and different embodiments and its several details are capable of modification in various other respects, all without departing from the spirit and scope of the invention. Accordingly, the drawings and detailed description are to be regarded as illustrative in nature and not as restrictive.

BRIEF DESCRIPTION OF THE DRAWINGS

Aspects of the microstimulator injection devices and systems are illustrated by way of example, and not by way of limitation, in the accompanying drawings, wherein.

DETAILED DESCRIPTION

Figure 1:
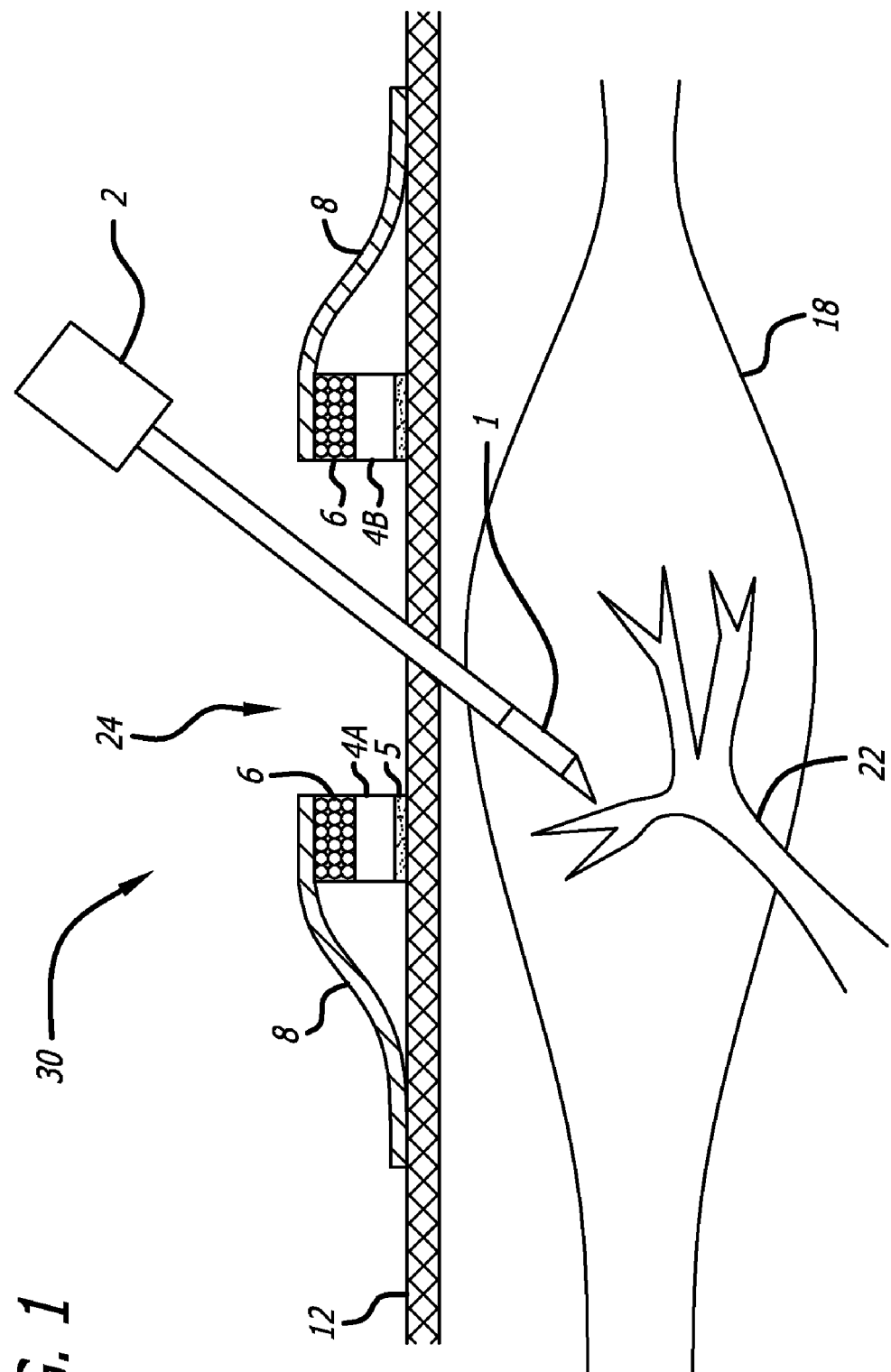
FIG. 1 is a side cross-sectional illustration of an exemplary microstimulator injection system.

The detailed description set forth below in connection with the appended drawings is intended as a description of exemplary embodiments and is not intended to represent the only embodiments in which the microstimulator injection devices, methods and systems can be practiced. The term "exemplary" used throughout this description means "serving as an example, instance, or illustration," and should not necessarily be construed as preferred or advantageous over other embodiments. The detailed description includes specific details for the purpose of providing a thorough understanding of the microstimulator injection devices, methods and systems. However, it will be apparent to those skilled in the art that the microstimulator injection devices, methods and systems may be practiced without these specific details.

The exemplary embodiments of the devices, systems and methods described herein can be used to locate a target site for the electrical stimulation, through a microstimulator, of nerves and muscles. The intensity of a search stimulus can be varied continuously near the threshold to evoke an M-wave, which is recorded by EMG electrodes. A feedback signal allows the clinician to judge when the threshold is sufficiently low to warrant the implantation of the stimulation electrodes at that site.

One example of an implant which may be useful in this invention is the BION™ (BIONic Neurons; Alfred E. Mann Institute, University of Southern California). BIONS™ are a new class of implantable medical device: separately addressable (up to 256), single channel, electronic microstimulators (16 mm long×2 mm in diameter), that can be injected in or near muscles and nerves to treat paralysis, spasticity and other neurological dysfunctions. Microstimulators that may be used in various embodiments are described in U.S. Pat. Nos. 5,193,539; 5,193,540; 5,312,439; and 5,324,316, each of which are incorporated by reference in their entirety. A BION typically may include a tantalum electrode at one end and an iridium electrode at the opposite end. Each BION™ may receive power and digital command data by a radio frequency electromagnetic field to produce functional or therapeutic electrical stimulation. A BION typically may include a tantalum electrode at one end and an iridium electrode at the opposite end. For use in this invention, the electrodes may be configured for selective interaction with the surfaces of an injection device, including but not limited to the cannula lumen or probe distal end for example.

Kaplan and Loeb teach the use of a specialized tool for inserting BION microstimulators (for example, U.S. patent application Ser. No. 10/461,560, filed Jun. 12, 2003, entitled "Injection Devices and Methods for Testing Implants"; and U.S. patent application Ser. No. 10/461,132, filed Jun. 12, 2003, entitled "Injection Devices and Methods for Unimpeded Target Location Testing," both of which are incorporated herein by reference). These wireless, self-contained modules may be controlled by telemetry from an external transmission coil that should be located in the vicinity of the implants. The insertion tool may provide means to hold an implant in the tip of the tool and holes to permit stimulation pulses emitted by the implant to pass through the adjacent tissues. The transmission coil may provide a physical platform on which surface electromyographic (EMG) electrodes can be positioned against the skin overlying the implantation site so that they can record the M-wave evoked by each stimulation pulse. The M-wave generally represents the propagation of action potentials along the surface of the muscle fibers that have been synaptically activated by stimulation of their innervating motor axons. The M-wave's amplitude tends to vary with the numbers of motor axons that are activated more or less synchronously by the stimulating pulse. The M-wave generally occurs between 1-5 ms after the stimulation pulse, which also produces a brief (<1 ms) shock artifact that can be recorded similarly by the EMG electrodes but with essentially zero delay from the stimulating pulse. It may also be possible to record the M-wave via intramuscular electrodes, such as on or within the shank of the insertion tool or even via the stimulating electrodes themselves, if the implant is equipped with the necessary amplification, processing and back-telemetry equipment. By measuring the amplitude of the M-wave, the stimulation intensity can be adjusted after each response to keep its intensity near the threshold for evoking an M-wave. The instrument may provide feedback on the stimulation intensity by emitting an acoustic tone pip whose pitch is proportional to the stimulus intensity. The clinician may use changes in the pitch of the tone pip to judge whether he/she is approaching or leaving the vicinity of a muscle nerve. Alternative devices and systems for providing feedback known to those skilled in the art may be used in various embodiments. The clinician may determine which of several possible nerves and muscles might be being activated by observing qualitatively the locus and effect of muscle contraction.

Referring to FIG. 1, an exemplary embodiment of the device 30 is affixed to the patient's skin 12 over the approximate target site for implantation of the microstimulator 1 via insertion tool 2. The clinician's goal typically is to position and deposit microstimulator 1 close to a nerve 22 that innervates the muscle 18. Microstimulator 1 can receive commands via antenna 6 that may controls the strength and timing of the electrical stimulation pulses that it emits. EMG electrodes 4A and 4B may be attached to antenna 6 to detect the M-wave produced by the muscle 18 when it is activated by stimulation of the nerve 22. Drape 8 attached to antenna 6 can provide a sterile field and has an aperture 24, through which the insertion tool 2 enters the skin 12. Advantageously, adhesive 5 may provide an electrically conductive and mechanically adhesive interface between electrodes 4A and 4B, thereby anchoring the entire assembly, including antenna 6 and drape 8, to the skin over the target site.

Figure 2:
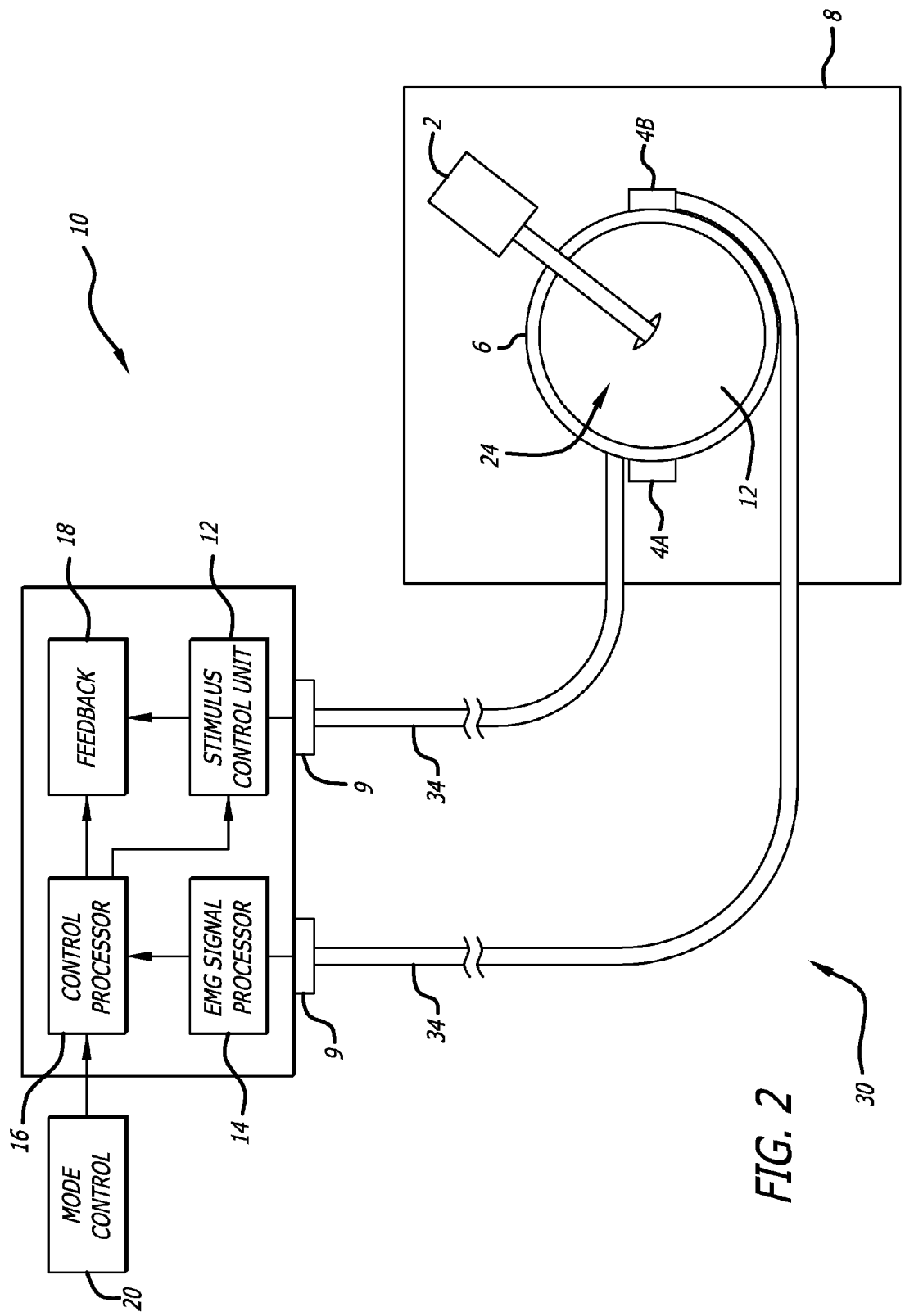
FIG. 2 is a schematic illustration of an exemplary microstimulator system and a top-down view of an exemplary microstimulator injection system.
Figure 3:
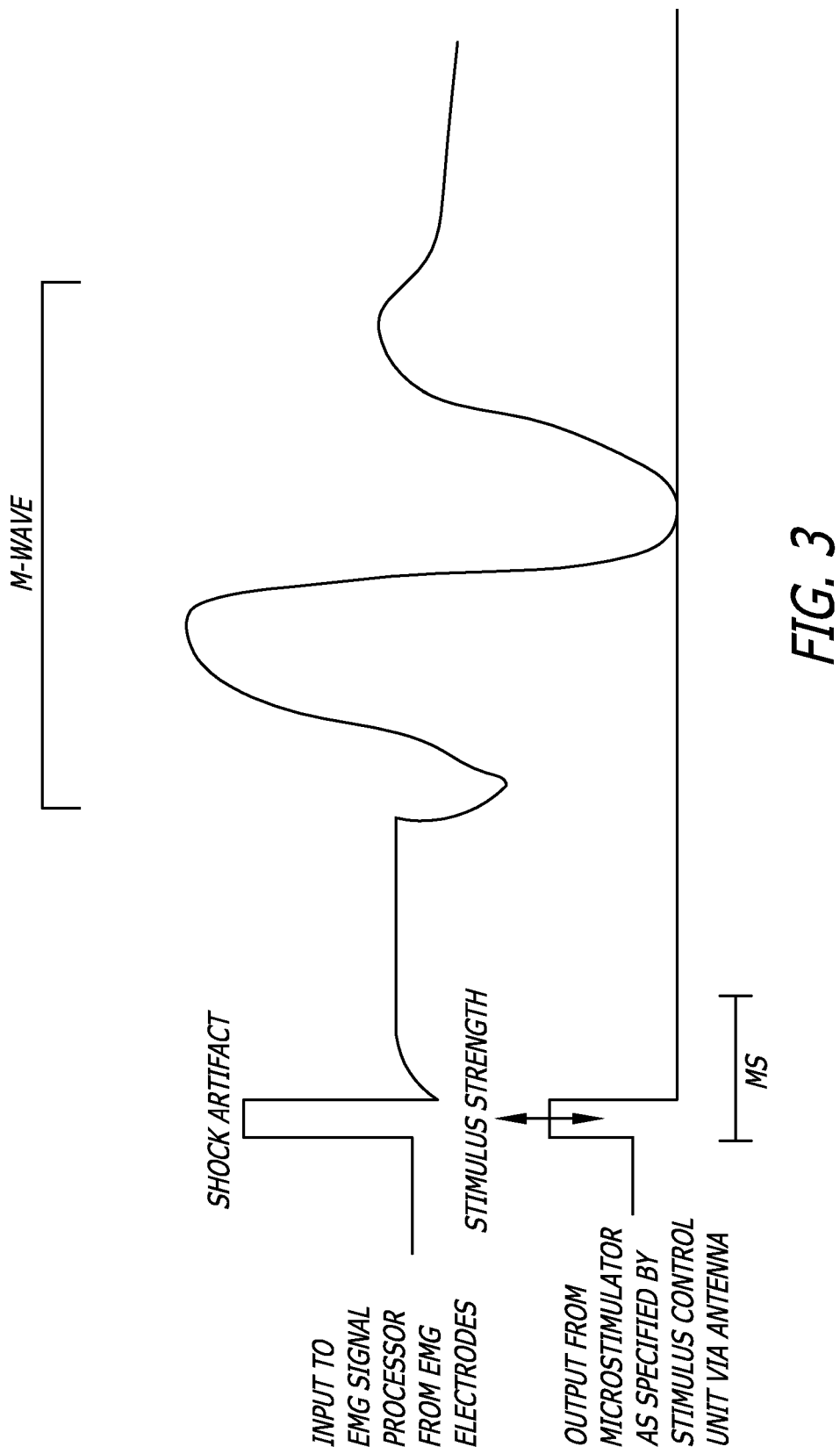
FIG. 3 is graph indicating basic input and output signals of an exemplary controller.

Referring to FIG. 2, the electrical leads 34 from antenna 6 and electrodes 4A and 4B can terminate in connectors 9 that provide electrical connection to the controller 10. The electrodes 4A, 4B, antenna 6, drape 8, connectors 9, and electrical leads 34 may collectively constitute a disposable assembly, which can be sterilized prior to use and discarded after use. Controller 10 may consist of a stimulus control unit 12, an EMG signal processor 14, control processor 16 and feedback 18, all of which can be embodied in conventional analog and/or digital electronic devices well-known to those skilled in the art such as amplifiers, digitizers, microprocessors, oscillators, modulators, loudspeakers, switches, etc. The basic input and output signals for controller 10 are illustrated in FIG. 3. Controller 10 may also receive input from mode control 20, which can be a mechanical hand or footswitch or a voice-activated control or other means known to those skilled in the art.

In an exemplary embodiment of a method of identifying a target site for injection of a microstimulator, the clinician may identify the approximate target site according to anatomical landmarks and prepared the skin in this region for an aseptic insertion procedure. The device may be affixed to the skin over the approximate target site by means of an adhesive and such other mechanical attachment aids as known to someone skilled in the art. An insertion tool containing a microstimulator at its distal tip is typically inserted into the patient's skin, aiming at the target site. The clinician can use the mode control to cause the controller to begin gradually increasing the strength of the stimulation pulses emitted by the microstimulator according to an algorithm used by the control processor. This may be accomplished by transmitting the appropriate commands to microstimulator from the stimulus control unit via the antenna.

The control processor may receive information from the EMG signal processor about the electrical signals recorded by the EMG electrodes, which are illustrated in the top trace of FIG. 3. The features of this signal generally include a shock artifact that occurs at the time of each stimulus pulse emitted by the microstimulator, followed by an M-wave, which is generated a few milliseconds later by any muscle fibers that have been activated as a result of the stimulus pulse.

The area under the curve of the M-wave is generally proportional to the total cross-sectional area of the muscle fibers that have been activated as a result of the stimulus pulse. Threshold stimulus strength is typically defined as the value that produces a detectable M-wave. Stimulus threshold can be varied either by changing the amplitude (as illustrated) or the duration (over a limited range, not illustrated) of the stimulus pulse, as is well-known in the art.

The control processor may continuously adjust the stimulus strength of each successive stimulus pulse using an algorithm so as to maintain the intensity near the threshold at the moment. As the microstimulator is advanced toward the nerve, the threshold will typically decline; if it is going away from the nerve, the threshold will increase. The control processor can receive information about the M-wave elicited by the stimulation and produced by the muscle. For example, various stimulation and feedback control systems that may be used are described in U.S. Pat. No. 5,775,331 to Raymond et al; U.S. Pat. No. 6,306,100 to Prass; U.S. Pat. No. 5,284,154 to Raymond et al; U.S. Pat. No. 6,259,945 to Epstein et al; U.S. Pat. No. 6,027,456 to Feler et al; U.S. Pat. No. 6,533,732 to Urmey et al; and U.S. Pat. No. 6,325,764 to Griffith et al; the contents of each of which are incorporated herein by reference.

The control processor may cause feedback to produce a percept that the clinician can detect and that has a property that can be made proportional to stimulus strength. For example, feedback can be an acoustic tone pip generated by a loudspeaker whose frequency or loudness is the variable property, or a light whose color or brightness is the variable property.

When the clinician determines that the microstimulator 1 is located so as to give a local minimum in threshold, it may also be advantageous to determine the recruitment curve for this site before releasing microstimulator. This is because it is possible that microstimulator is actually located near a small branch of the nerve in the muscle but is not located sufficiently close to the main nerve so as to be able to activate all of the muscle. It is also possible that it is located close to another nerve whose effects are undesirable when stimulated. Therefore, the clinician may use the mode control to cause the control processor to gradually ramp up the stimulus strength above threshold while it records the amplitude of the M-waves being evoked. The clinician can observe the growing strength of the contractions and compare them to the strength of the stimulus pulses and the amplitude of the M-wave, for example by viewing a graphical display device that is part of or driven by the controller, as is well-known in the art. Advantageously, the control processor may determine when the M-waves reach maximal amplitude, representing full recruitment of the target Muscle (also called "saturation"), and turn the stimulation off.

When the clinician determines that microstimulator is located in the appropriate target site, it is typically released from insertion tool, which is withdrawn from the body. The device may be detached from controller by means of the connectors and may be discarded or resterilized for reuse.

The EMG and reference electrode may be attached to the drape. Alternatively, the EMG electrode may be attached to the antenna. The EMG electrode may also be located on or in the microstimulator. For example, small electrode contacts may be mounted on the surface of the shank of insertion tool 2, near or proximal to microstimulator 1. They may also be coextensive with the electrodes of microstimulator 1 itself if the microstimulator is equipped to measure EMG and telemeter out the results of its measurement, or they may be on another microstimulator so equipped that had been injected previously in the region. These internal locations may be more sensitive to locally produced M-waves and less sensitive to extraneous electrical noise, which is sometimes a problem with skin surface electrodes. One advantage of the relatively widely spaced skin electrodes 4A and 4B illustrated in FIGS. 1 and 2 is that they would tend to sample widely from many possible muscle targets rather than just the one in the immediate vicinity of closely spaced electrodes. Normally this is not considered desirable for EMG recordings because the usual goal is to record selectively from one muscle in the presence of simultaneous activity from multiple muscles. However, in some cases the patient may be relaxed and a useful source of EMG to be recorded arises from the M-waves elicited by the stimulation.

Figure 4:
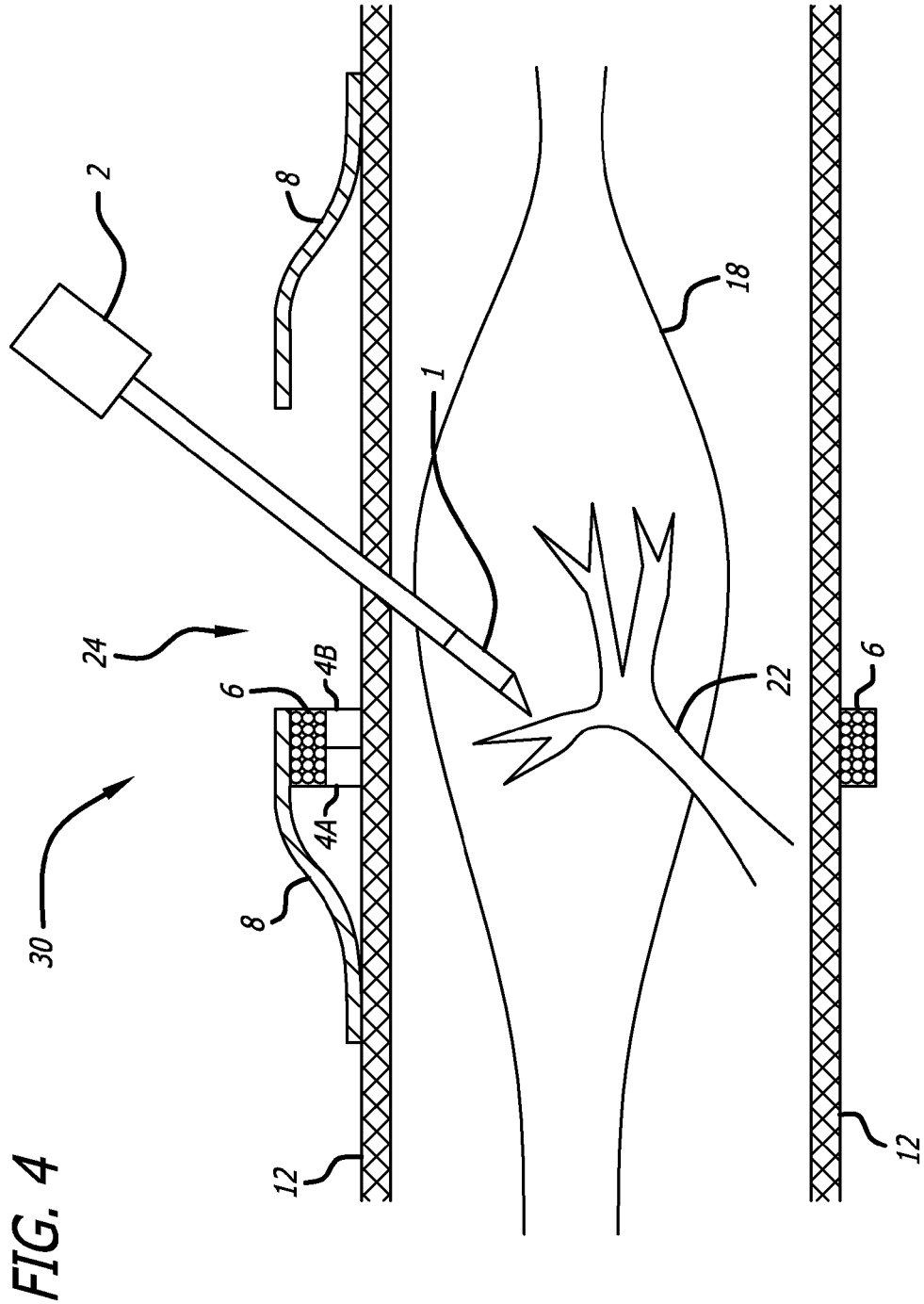
FIG. 4 is a side cross-sectional illustration of another exemplary microstimulator injection system.

For use in distal limb locations such as the forearm, it may be advantageous to orient antenna 6 transversely to the axis of the limb, i.e. like a bracelet. In that configuration, EMG recording electrodes 4A and 4B may be located on the inside circumference of antenna 6 and drape 8 may be attached to a portion of the outside circumference of antenna 6, as illustrated in FIG. 4. Note, however, that this produces the opposite effect from the orientation illustrated in FIGS. 1 and 2, in terms of controlling the relative orientation of the axis of the microstimulator vis-à-vis the field produced by the antenna. This may particularly benefit microstimulators that receive both their power and their stimulus commands from the antenna. The microstimulator may contain a receiving antenna which is actually a cylindrical inductive coil oriented parallel to the long axis of the microstimulator. This may function as the secondary winding of a power transformer whose primary winding is the externally worn antenna coil. If the antenna is a flat coil as illustrated, the flux lines around it tend to be in the shape of a torus, i.e., they tend to be oriented differently in different places around the coil. The efficiency of power transfer between the primary and secondary windings tends to be highest if the secondary is parallel to the flux lines created by the primary. At the extreme of misalignment (orthogonality), there may be a null for which no power (and hence, no data) can be transmitted between the two.

In the exemplary embodiments illustrated in FIGS. 1 and 2, an insertion that starts in the middle of the aperture 24 of drape 8 (which in some embodiments corresponds to the middle of the antenna 6) and is oriented normal to the skin surface may tend to follow the orientation of flux lines, which may be normal to the plane of the coil in the center of the coil. An insertion that starts in the middle of the opening of the drape but is oriented obliquely to the surface of the skin and the plane of the coil will tend to pass under the edge of the coil in an orientation that is closer to parallel to the plane of the coil. The flux lines passing around the circumference of the coil can be parallel to the plane of the coil in this region. Thus there may be a natural tendency for the microstimulator to be reasonably well-aligned with the flux lines created by the antenna for any angle of insertion elected by the clinician. The converse tends to be true for the configuration illustrated in FIG. 4.

The previous description of the disclosed embodiments is provided to enable any person skilled in the art to make or use the microstimulator injection devices, methods and systems. Various modifications to these embodiments will be readily apparent to those skilled in the art, and the generic principles defined herein may be applied to other embodiments without departing from the spirit or scope of the microstimulator injection devices, methods and systems. Thus, the microstimulator injection devices, methods and systems are not intended to be limited to the embodiments shown herein but are to be accorded the widest scope consistent with the principles and novel features disclosed herein.

What is claimed is:

1. A device for identifying a target site for implanting a microstimulator in a patient's body, comprising:

a drape having an aperture;

an injection device containing a microstimulator:
  a transmitting antenna affixed to and located underneath the drape and that encircles an area of the body defined by the aperture, wherein the antenna is capable of creating an inductive field to control the microstimulator while the injection device and microstimulator are positioned within the patient's body;
    at least one electromyographic electrode affixed to and located underneath the antenna, wherein the at least one electromyographic electrode is capable of detecting M-waves produced by the patient's body; and
    an electrically conductive adhesive material located underneath the at least one electromyographic electrode.

2. The device of claim 1, wherein the antenna is substantially aligned with the perimeter of the aperture.

3. A system for implanting a microstimulator in a patient's body, comprising:
  a drape having an aperture;
  an injection device containing a microstimulator, wherein the microstimulator is capable of stimulating at least one nerve, while the injection device containing the microstimulator is positioned within the patient's body;
  a transmitting antenna affixed to and located underneath the drape and that encircles an area of the body defined by the aperture, wherein the antenna is capable of creating an inductive field to control the microstimulator while the injection device and microstimulator are positioned within the patient's body;
  at least one electrode affixed to and located underneath the antenna, wherein the at least one electromyographic electrode is capable of detecting M-waves produced by the patient's body;
  an electrically conductive adhesive material located underneath the at least one electromyographic electrode; and
  a controller, wherein the controller is capable of providing microstimulator-control signals to the transmitting antenna, and receiving and analyzing information from the M-waves detected by the at least one electrode.

4. The system of claim 3, wherein the antenna is substantially aligned with the perimeter of the aperture.

5. The system of claim 3, wherein the antenna is capable of receiving information about the detected M-waves from the microstimulator, and is capable of transmitting the information to the controller.

6. The system of claim 3, wherein the controller comprises an EMG signal processor, a stimulus control unit, control processor, and a feedback unit.

7. The system of claim 3, wherein the controller is further capable of providing additional signals to the antenna based on the received and analyzed information from the detected M-waves.

* * * * *